United States Patent
Torii et al.

(10) Patent No.: US 11,360,034 B2
(45) Date of Patent: Jun. 14, 2022

(54) RADIATION IMAGING APPARATUS AND RADIATION IMAGING SYSTEM

(71) Applicant: CANON KABUSHIKI KAISHA, Tokyo (JP)

(72) Inventors: Sota Torii, Kawasaki (JP); Kosuke Terui, Yokohama (JP); Akira Tsukuda, Kawasaki (JP); Atsushi Iwashita, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 299 days.

(21) Appl. No.: 16/745,807

(22) Filed: Jan. 17, 2020

(65) Prior Publication Data
US 2020/0150059 A1    May 14, 2020

Related U.S. Application Data

(63) Continuation of application No. PCT/JP2018/025492, filed on Jul. 5, 2018.

(30) Foreign Application Priority Data

Aug. 25, 2017   (JP) ............................ JP2017-162693

(51) Int. Cl.
*G01N 23/04* (2018.01)
*A61B 6/00* (2006.01)
(Continued)

(52) U.S. Cl.
CPC ........... *G01N 23/04* (2013.01); *A61B 6/4233* (2013.01); *A61B 6/5258* (2013.01); *G06T 5/002* (2013.01);
(Continued)

(58) Field of Classification Search
CPC .... A61B 6/4233; A61B 6/5258; G01N 23/04; G01N 2223/424; G06T 5/002; G06T 5/50;
(Continued)

(56) References Cited

U.S. PATENT DOCUMENTS 7,711,082 B2   5/2010  Fujimoto
7,756,240 B2   7/2010  Nishide
(Continued)

FOREIGN PATENT DOCUMENTS

JP   S63-049142   3/1988
JP   2007-000407  1/2007
(Continued)

OTHER PUBLICATIONS

U.S. Appl. No. 16/103,150, Atsushi Iwashita, filed Aug. 14, 2018.
(Continued)

*Primary Examiner* — Mark R Gaworecki
(74) *Attorney, Agent, or Firm* — Venable LLP

(57) ABSTRACT

A radiation imaging apparatus is provided. The apparatus includes an imaging unit including pixels and a control unit. Each of the pixels includes a conversion unit and a sample/hold circuit. The control unit causes the imaging unit to perform first imaging and second imaging after the first imaging to generate one energy subtraction image, and controls a timing of causing the sample/hold circuit in the first imaging to sample a first image signal obtained by the first imaging and a timing of causing the sample/hold circuit in the second imaging to sample a second image signal obtained by the second imaging in accordance with radiation irradiation conditions set in advance so as to reduce a difference between an amount of noise contained in the first image signal and an amount of noise contained in the second image signal.

20 Claims, 8 Drawing Sheets

(51) Int. Cl.
- *G06T 5/00* (2006.01)
- *G06T 5/50* (2006.01)
- *H04N 5/32* (2006.01)
- *H04N 5/3745* (2011.01)

(52) U.S. Cl.
CPC ............. *G06T 5/50* (2013.01); *H04N 5/3205* (2013.01); *H04N 5/37452* (2013.01); *G01N 2223/424* (2013.01); *G06T 2207/10116* (2013.01); *G06T 2207/20182* (2013.01); *G06T 2207/20224* (2013.01); *G06T 2207/30004* (2013.01)

(58) Field of Classification Search
CPC . G06T 2207/10116; G06T 2207/20182; G06T 2207/20224; G06T 2207/30004; H04N 5/3205; H04N 5/3559; H04N 5/37452
See application file for complete search history.

(56) References Cited

U.S. PATENT DOCUMENTS

| | | |
|---|---|---|
| 9,048,154 B2 | 6/2015 | Takenaka et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,812,474 B2 | 11/2017 | Yagi et al. |
| 9,820,711 B2 | 11/2017 | Tsukuda |
| 9,820,712 B2 | 11/2017 | Takasaki |
| 9,971,046 B2 | 5/2018 | Ryu et al. |
| 9,980,685 B2 | 5/2018 | Iwashita et al. |
| 9,989,656 B2 | 6/2018 | Sato et al. |
| 10,009,990 B2 | 6/2018 | Takenaka et al. |
| 10,070,082 B2 | 9/2018 | Tsukuda |
| 10,197,684 B2 | 2/2019 | Terui et al. |
| 10,274,612 B2 | 4/2019 | Ishii et al. |
| 10,441,238 B2 | 10/2019 | Terui et al. |
| 2009/0180585 A1 | 7/2009 | Fujimoto |
| 2014/0239186 A1 | 8/2014 | Sato et al. |
| 2014/0361189 A1 | 12/2014 | Kameshima et al. |
| 2015/0001394 A1 | 1/2015 | Yamazaki |
| 2015/0055752 A1* | 2/2015 | Takahashi ................ H04N 5/32 378/62 |
| 2015/0189194 A1* | 7/2015 | Tajima .................. A61B 6/488 378/62 |
| 2016/0270755 A1 | 9/2016 | Takenaka et al. |
| 2018/0128755 A1 | 5/2018 | Iwashita et al. |
| 2018/0317868 A1 | 11/2018 | Terui et al. |
| 2018/0328862 A1 | 11/2018 | Sato et al. |
| 2019/0179036 A1 | 6/2019 | Takenaka et al. |
| 2019/0320993 A1 | 10/2019 | Noda et al. |
| 2019/0349541 A1 | 11/2019 | Iwashita et al. |
| 2020/0124749 A1 | 4/2020 | Takenaka et al. |

FOREIGN PATENT DOCUMENTS

| | | |
|---|---|---|
| JP | 2008-148886 A | 7/2008 |
| JP | 2009-504221 | 2/2009 |
| JP | 2009-82174 A | 4/2009 |
| JP | 2009-131464 A | 6/2009 |
| JP | 2010-75555 A | 4/2010 |
| JP | 2010-82321 A | 4/2010 |
| JP | 2010-284350 A | 12/2010 |
| JP | 2011-78103 A | 4/2011 |
| JP | 2011-152280 A | 8/2011 |
| JP | 2013-5896 A | 1/2013 |
| JP | 2017-73756 A | 4/2017 |
| WO | 2007/017773 | 2/2007 |

OTHER PUBLICATIONS

U.S. Appl. No. 16/731,143, Kosuke Terui, filed Dec. 31, 2019.
U.S. Appl. No. 16/749,201, Sota Torii, filed Jan. 22, 2020.
U.S. Appl. No. 16/813,970, Atsushi Iwashita, filed Mar. 10, 2020.
U.S. Appl. No. 16/847,074, Akira Tsukuda, filed Apr. 13, 2020.

* cited by examiner

| BODY THICKNESS | IRRADIATION CONDITION | |
|---|---|---|
| | HIGH-ENERGY IMAGE | LOW-ENERGY IMAGE |
| THIN | 140kV 10mA 10ms | 100kV 50mA 20ms |
| NORMAL | 140kV 10mA 20ms | 100kV 70mA 40ms |
| THICK | 140kV 10mA 40ms | 100kV 90mA 80ms |

RADIATION IMAGING APPARATUS AND RADIATION IMAGING SYSTEM

CROSS-REFERENCE TO RELATED APPLICATIONS

This application is a Continuation of International Patent Application No. PCT/JP2018/025492, filed Jul. 5, 2018, which claims the benefit of Japanese Patent Application No. 2017-162693, filed Aug. 25, 2017, both of which are hereby incorporated by reference herein in their entirety.

BACKGROUND OF THE INVENTION

Field of the Invention

The present invention relates to a radiation imaging apparatus and a radiation imaging system.

Background Art

A radiation imaging apparatus using an FPD (flat panel detector) formed from a semiconductor material is widely used in medical image diagnosis and non-destructive inspection. As one type of imaging method using such an FPD, there is known a method of obtaining an energy subtraction image by using radiations having different energy components. The time interval at which a plurality of radiation images are obtained by imaging is several sec or more in a radiation imaging apparatus for still images, about 100 msec in a radiation imaging apparatus for normal moving images, and about 10 msec in a radiation imaging apparatus for fast moving images. When an object moves during this time interval, the movement of the object causes artifacts. Accordingly, it is difficult to obtain an energy subtraction image of a fast moving object such as the heart. PTL 1 discloses a technique of obtaining an energy subtraction image of a fast moving object by transferring a first imaging signal to a sample/hold node and then reading out the first signal from the sample/hold node while accumulating a second imaging signal. The X-ray imaging system disclosed in PTL 1 concurrently performs reading out of a first imaging signal and accumulation of a second imaging signal to shorten the interval between the two imaging operations, thereby obtaining an energy subtraction image of a fast moving object.

CITATION LIST

Patent Literature

PTL 1: Japanese Patent Laid-Open No. 2009-504221

The noise contained in an energy subtraction image depends on the amounts of noise in a radiation image obtained by imaging with high-energy radiation and a radiation image obtained by imaging with low-energy radiation. In order to improve the image quality of an energy subtraction image, it is necessary to consider the amounts of noise respectively contained in a high-energy image and a low-energy image. PTL 1 makes no reference to the amounts of noise contained in signals obtained by the respective imaging operations.

The present invention has an object to provide a technique advantageous in improving the image quality of an energy subtraction image in a radiation imaging apparatus.

SUMMARY OF THE INVENTION

According to some embodiments, a radiation imaging apparatus including an imaging unit including a plurality of pixels and a control unit, wherein each of the plurality of pixels includes a conversion unit configured to generate an image signal corresponding to incident radiation and a sample/hold circuit configured to hold an image signal generated by the conversion unit, and the control unit causes the imaging unit to perform first imaging and second imaging after the first imaging to generate one energy subtraction image, and controls a timing of causing the sample/hold circuit in the first imaging to sample a first image signal obtained by the first imaging and a timing of causing the sample/hold circuit in the second imaging to sample a second image signal obtained by the second imaging in accordance with radiation irradiation conditions set in advance so as to reduce a difference between an amount of noise contained in the first image signal and an amount of noise contained in the second image signal, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DESCRIPTION OF THE EMBODIMENTS

Specific embodiments of a radiation imaging apparatus according to the present invention will be described below with reference to the accompanying drawings. Note that radiation according to the present invention can include not only α-rays, β-rays, and γ-rays that are beams generated by particles (including photons) emitted by radioactive decay but also beams having energy equal to or more than the energy of these beams, for example, X-rays, particle rays, and cosmic rays.

Figure 1:
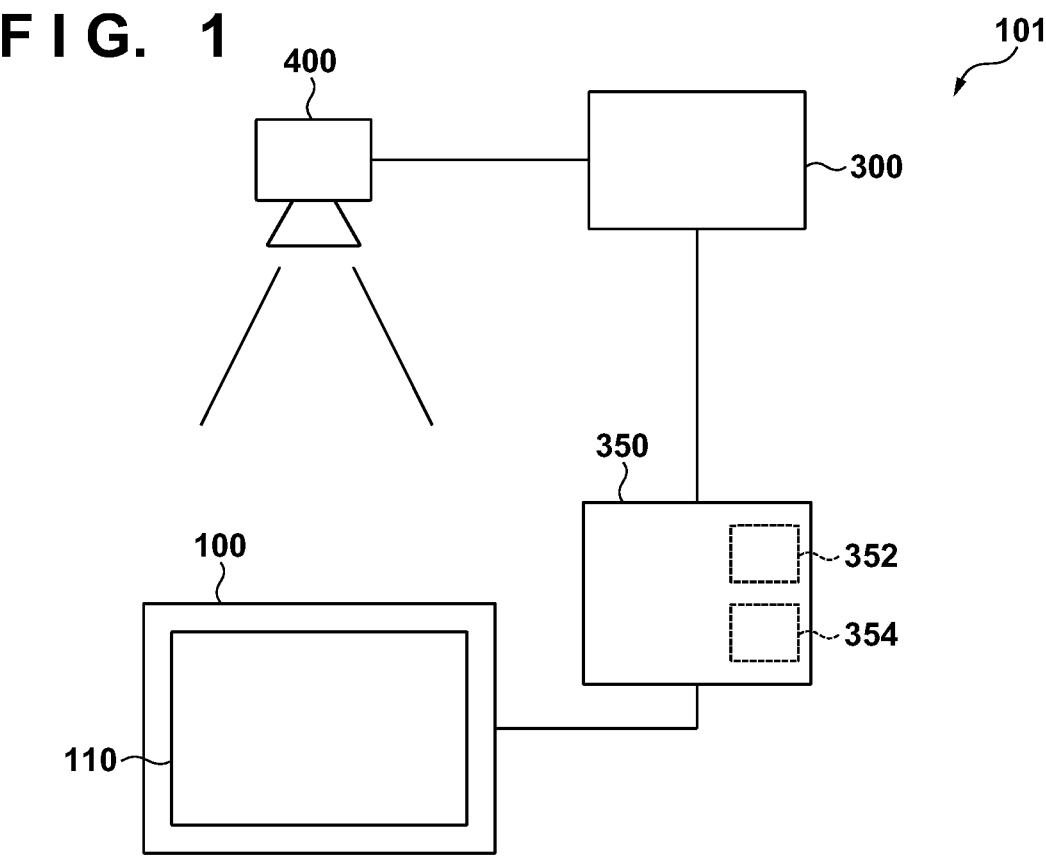
FIG. 1 is a block diagram showing an example of the arrangement of a radiation imaging system using a radiation imaging apparatus according to an embodiment of the present invention.

The arrangement and operation of a radiation imaging apparatus according to an embodiment of the present invention will be described with reference to FIGS. 1 to 6. FIG. 1 shows an example of the arrangement of a radiation imaging system 101 using a radiation imaging apparatus 100 according to the first embodiment of the present invention. In this embodiment, the radiation imaging system 101 using the radiation imaging apparatus 100 is a system for obtaining a radiation image by an energy subtraction method. The energy subtraction method is a method of processing a plurality of radiation images obtained by a plurality of times of imaging using radiations having different energies with respect to an object, thereby obtaining new radiation images (for example, a bone image and a soft tissue image). The radiation imaging system 101 is configured to obtain an electrical signal (image signal) for generating a radiation image by electrically obtaining an optical image by imaging, which is converted from radiation entering the radiation imaging apparatus 100.

The radiation imaging system 101 includes the radiation imaging apparatus 100, a radiation source 400 for irradiation with radiation, an exposure control unit 300 that controls the radiation source 400, and a system control unit 350 that controls the exposure control unit 300 (radiation source 400) and the radiation imaging apparatus 100.

The system control unit 350 can be constituted by a computer (processor) and a memory storing programs to be provided to the computer. The system control unit 350 also includes a signal processing unit 352 that processes signals supplied from the radiation imaging apparatus 100. The signal processing unit 352 can be formed from some of the programs stored in the memory of the system control unit 350. The signal processing unit 352 may be installed independently of the system control unit 350 and constituted by a computer (processor) and a memory storing programs to be provided to the computer. The system control unit 350 may be totally or partially formed from a DSP (digital signal processor) or PLA (programmable logic array). The system control unit 350 and the signal processing unit 352 may be designed and manufactured by a logic synthesis tool based on files describing its operations. The system control unit 350 may function as a user interface of the radiation imaging system 101. In this case, the system control unit 350 can include, for example, an input unit that allows the user to input imaging conditions for obtaining a radiation image and a display unit such as a display for checking input information.

The exposure control unit 300 controls irradiation with radiation by the radiation source 400. The exposure control unit 300 may have, for example, an exposure switch and notify the system control unit 350 of information indicating the timing of emitting radiation in addition to causing the radiation source 400 to emit radiation in response to turning on of the exposure switch by the user. The exposure control unit 300 may also cause the radiation source 400 to emit radiation in accordance with a command from the system control unit 350.

The radiation source 400 has a function of changing the energy (wavelength) of radiation. The radiation source 400 can change the energy of radiation by, for example, changing a tube voltage (a voltage to be applied between the cathode and the anode of the radiation source 400) under the control of the exposure control unit 300. The radiation source 400 can emit radiations having a plurality of energy values different from each other.

The radiation imaging apparatus 100 includes a pixel array 110 including a plurality of pixels. Each of the plurality of pixels includes a conversion unit that converts incident radiation into an electrical signal (for example, charge), a reset unit that resets the conversion unit, and a sample/hold circuit for holding image signals generated by the conversion unit. Each pixel may be configured to directly convert radiation into an electrical signal or to convert radiation into light such as visible light and then convert the converted light into an electrical signal. In the latter case, each pixel can use a scintillator for converting radiation into light. The scintillator can be shared by a plurality of pixels constituting the pixel array 110.

In the arrangement example shown in FIG. 1, the radiation imaging apparatus 100 and the system control unit 350 are arranged independently of each other. However, all or part of the function of the system control unit 350 may be incorporated in the radiation imaging apparatus 100. In addition, part of the function of the radiation imaging apparatus 100 may be incorporated in the system control unit 350.

Figure 2:
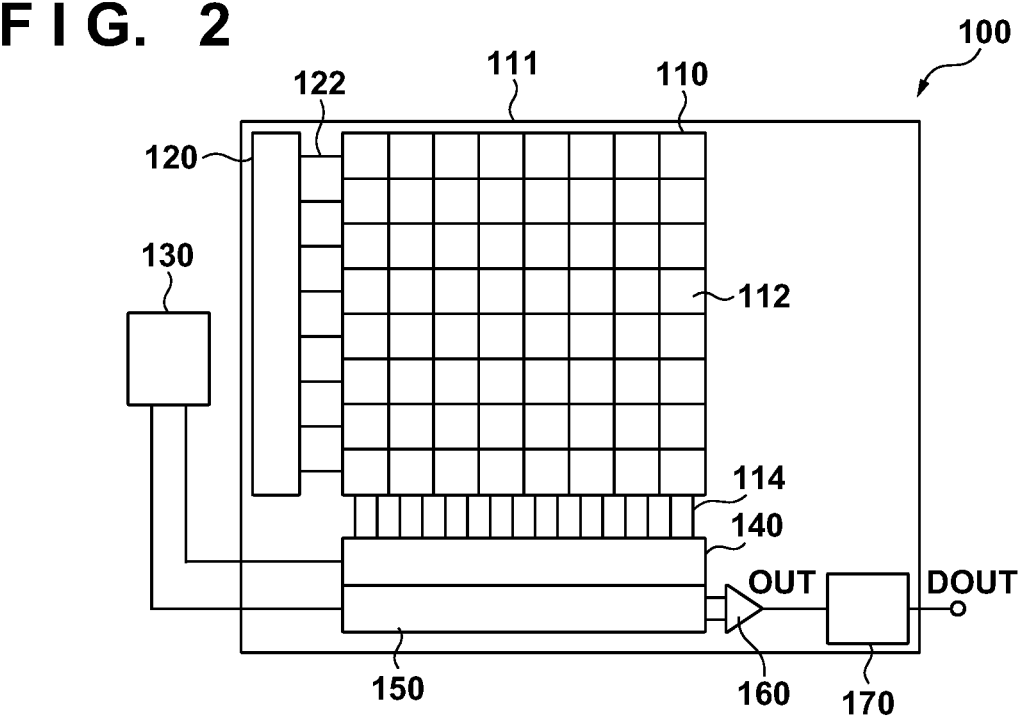
FIG. 2 is a block diagram showing an example of the arrangement of the radiation imaging apparatus in FIG. 1.

FIG. 2 shows an example of the arrangement of the radiation imaging apparatus 100. The radiation imaging apparatus 100 includes an imaging unit 111 and a control unit 130 for controlling the imaging unit 111. The imaging unit 111 includes the pixel array 110 having a plurality of pixels 112, a row selection circuit 120, a readout circuit 140, a column selection circuit 150, an amplification unit 160, and an AD conversion unit 170.

In the pixel array 110, the plurality of pixels 112 are arranged to form a plurality of rows and a plurality of columns in an array pattern. In the arrangement shown in FIG. 2, the pixel array 110 is constituted by the 8 row×8 column pixels 112. In practice, however, more pixels 112 can be arranged. For example, the pixel array 110 can have a dimension of 17 inches and about 3000 row×about 3000 column pixels 112.

The row selection circuit 120 selects a row, of the pixel array 110 in which the plurality of pixels 112 are arranged, which outputs signals. The row selection circuit 120 selects a row by driving a row control signal line 122. The readout circuit 140 reads out signals from the pixels 112 of the row, of the plurality of rows of the pixel array 110, which is selected by the row selection circuit 120. The readout circuit 140 reads out signals corresponding to a plurality of columns which are output to a plurality of column signal lines 114 of the pixel array 110. The column signal lines 114 of the respective columns can include, for example, a plurality of signal lines that transmit a plurality of image signals detected by the pixels 112. For example, image signals corresponding to the radiation detected by the pixels 112 and noise levels of thermal noise or the like of the pixels 112 can be respectively output to a plurality of signal lines included in the column signal lines 114. The readout circuit 140 can be configured to read out the respective image signals and noise levels output to the column signal lines 114. The column selection circuit 150 selects signals corresponding to a plurality of columns read out from the pixels 112 of the row of the pixel array 110 which is selected by the readout circuit 140 in a predetermined order. The amplification unit 160 amplifies the signals selected by the column selection circuit 150. In this case, when the readout circuit 140 reads out pairs of image signals and noise levels from the pixels 112, the amplification unit 160 may be configured as a differential amplifier that amplifies the difference between an image signal and a noise level forming a pair or to amplify each of them independently. The AD conversion unit 170 A/D-converts a signal OUT output from the amplification unit 160 and outputs the digital signal DOUT as an image signal. The control unit 130 controls the row selection circuit 120, the readout circuit 140, the column selection circuit 150, and the amplification unit 160, and causes the radiation imaging apparatus 100 to output the image signals generated by the pixels 112 arranged in the pixel array 110 of the imaging unit 111.

Figure 3:
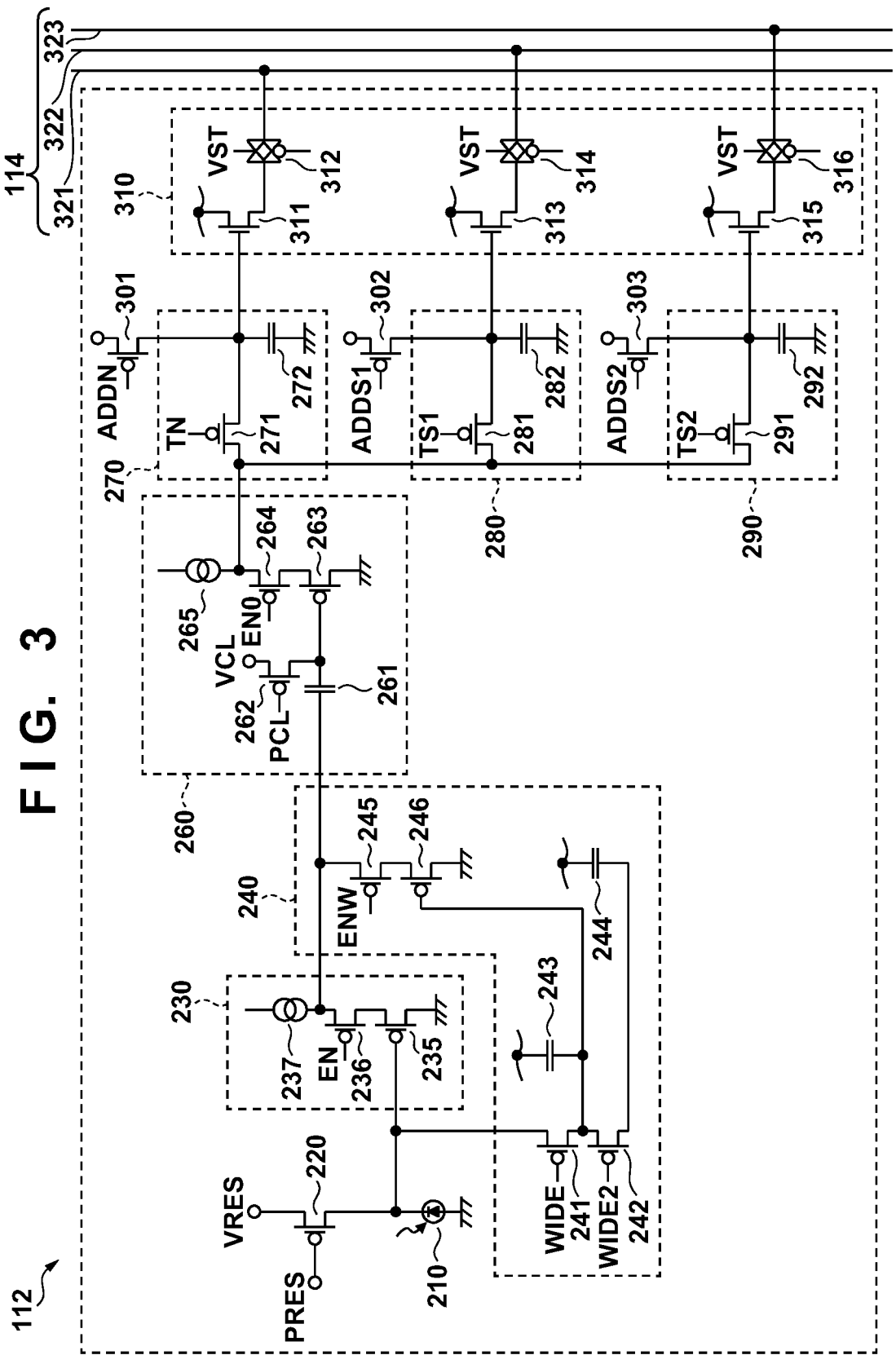
FIG. 3 is a circuit diagram showing an example of the arrangement of a pixel of the radiation imaging apparatus in FIG. 1.

FIG. 3 shows an example of the arrangement of one pixel 112 arranged in the pixel array 110. The pixel 112 includes a conversion element 210, a reset switch 220, an amplification circuit 230, a sensitivity changing unit 240, a clamp circuit 260, sample/hold circuits 270, 280, and 290, and an output circuit 310.

The conversion element 210 functions as a conversion unit that converts incident radiation into an electrical signal (image signal). The conversion element 210 can be constituted by a scintillator that converts radiation shared by a plurality of pixels into light and a photoelectric conversion element that converts converted light into an electrical signal. The conversion element 210 includes a charge accumulation unit that accumulates electrical signals (charge) converted from radiation, that is, electrical signals corresponding to radiation. The charge accumulation unit is connected to the input terminal of the amplification circuit 230.

The amplification circuit 230 includes transistors 235 and 236 and a current source 237. The transistor 235 is connected to the current source 237 via the transistor 236. The transistor 235 and the current source 237 constitute a source follower circuit. The transistor 236 is an enable switch that is turned on by activating an enable signal EN to activate the source follower circuit constituted by the transistor 235 and the current source 237. The charge accumulation unit of the conversion element 210 and the gate of the transistor 235 function as a charge voltage conversion unit CVC that converts the charge accumulated in the charge accumulation unit into a voltage. That is, a voltage V (=Q/C) determined by charge Q accumulated in the charge accumulation unit and a capacitance value C of the charge voltage conversion unit CVC appears in the charge voltage conversion unit CVC. The charge voltage conversion unit CVC is connected to a reset potential VRES via the reset switch 220. Activating a reset signal PRES will turn on the reset switch 220 to reset the potential VRES of the charge voltage conversion unit CVC to the reset potential VRES. The reset switch 220 can include a transistor having a first main electrode (drain) connected to the charge accumulation unit of the conversion element 210, a second main electrode (source) to which the reset potential VRES is applied, and a control electrode (gate). An ON voltage is applied to the control electrode of the transistor to render the first and second main electrodes conductive, thereby resetting the charge accumulation unit of the conversion element 210.

The clamp circuit 260 includes a clamp capacitor 261, transistors 262, 263, and 264, and a current source 265. The clamp circuit 260 clamps the reset noise level output from the amplification circuit 230 in accordance with the potential of the reset charge voltage conversion unit CVC by using the clamp capacitor 261. The clamp circuit 260 is a circuit for canceling a reset noise level from the image signal output from the amplification circuit 230 in accordance with the charge (electrical signal) converted by the conversion element 210. A reset noise level includes kTC noise when the charge voltage conversion unit CVC is reset. A clamp operation is performed by turning on the transistor 262 by activating a clamp signal PCL and then turning off the transistor 262 by inactivating the clamp signal PCL. The output side of the clamp capacitor 261 is connected to the gate of the transistor 263. The source of the transistor 263 is connected to the current source 265 via the transistor 264. The transistor 263 and the current source 265 constitute a source follower circuit. The transistor 264 is an enable switch that is turned on by activating an enable signal ENO supplied to the gate of the transistor 264 to activate the source follower circuit constituted by the transistor 263 and the current source 265.

The output circuit 310 includes transistors 311, 313, and 315 and row selection switches 312, 314, and 316. The transistors 311, 313, and 315 form source follower circuits together with current sources (not shown) respectively connected to signal lines 321, 322, and 323 of the column signal lines 114.

The sample/hold circuit 280 can hold (sample/hold) the image signal output from the clamp circuit 260 in accordance with the charge generated by the conversion element 210. The sample/hold circuit 280 includes a switch 281 and a capacitor 282. The switch 281 is turned on by activating a sample/hold signal TS1. The image signal output from the clamp circuit 260 is written in the capacitor 282 via the switch 281 by activating the sample/hold signal TS1. In the arrangement shown in FIG. 3, the pixel 112 can include an additional sample/hold circuit 290 for writing image signals. The sample/hold circuit 290 may sample an image signal different from the image signal sampled by the sample/hold circuit 280. The sample/hold circuit 290 can sample/hold the image signal output from the clamp circuit 260 in accordance with the charge generated by the conversion element 210. The sample/hold circuit 290 includes a switch 291 and a capacitor 292. The switch 291 is turned on by activating a sample/hold signal TS2. The image signal output from the clamp circuit 260 is written in the capacitor 292 via the switch 291 by activating the sample/hold signal TS2. The pixel 112 may further have an additional sample/hold circuit for writing image signals. That is, the pixel 112 may have an arbitrary number of sample/hold circuits for writing image signals. While the potential of the charge voltage conversion unit CVC is reset by the reset switch 220 and the transistor 262 is turned on, the clamp circuit 260 outputs the noise level (offset component) of thermal noise or the like in the clamp circuit 260. The sample/hold circuit 270 can sample/hold the noise level of the clamp circuit 260. The sample/hold circuit 270 includes a switch 271 and a capacitor 272. The switch 271 is turned on by activating a sample/hold signal TN. The noise level output from the clamp circuit 260 is written in the capacitor 272 via the switch 271 by activating the sample/hold signal TN. In this embodiment, the sample/hold circuit 270 may also be used to hold a radiation signal as a signal output from the clamp circuit 260 in accordance with the charge generated by the conversion element 210. When a row selection signal VST is activated, the signals held in the sample/hold circuits 270, 280, and 290 are respectively output to the signal lines 321, 322, and 323 constituting the column signal lines 114. More specifically, a signal N corresponding to a signal (noise level or image signal) held by the sample/hold circuit 270 is output to the signal line 321 via the transistor 311 and the row selection switch 312. A signal S1 corresponding to an image signal held by the sample/hold circuit 280 is output to the signal line 322 via the transistor 313 and the row selection switch 314. A signal S2 corresponding to an image signal held by the sample/hold circuit 290 is output to the column signal line 323 via the transistor 315 and the row selection switch 316.

The pixel 112 may include addition switches 301, 302, and 303 for adding signals among the plurality of pixels 112. In an addition mode in which signals are added among the plurality of pixels 112, addition mode signals ADDN, ADDS1, and ADDS2 are activated. Activating the addition mode signal ADDN will connect the capacitors 272 of the plurality of pixels 112 to each other, thereby averaging the signals. Activating the addition mode signal ADDS1 will connect the capacitors 282 of the plurality of pixels 112 to each other, thereby averaging the signals. Activating the addition mode signal ADDS2 will connect the capacitors 292 of the plurality of pixels 112 to each other, thereby averaging the signals.

The pixel 112 can include the sensitivity changing unit 240. The sensitivity changing unit 240 includes switches 241 and 242, capacitors 243 and 244, and transistors 245 and 246. Activating a change signal WIDE will turn on the switch 241 to add the capacitance value of the capacitor 243 to the capacitance value of the charge voltage conversion unit CVC. This decreases the sensitivity of the pixel 112. When the change signal WIDE is activated, an enable signal ENW may be activated. In addition, activating a change signal WIDE2 will turn on the switch 242 to add the capacitance value of the capacitor 244 to the capacitance value of the charge voltage conversion unit CVC. This further decreases the sensitivity of the pixel 112. The dynamic range can be widened by adding a function of decreasing the sensitivity of the pixel 112. The number of capacitors arranged in the sensitivity changing unit 240 may be one or three or more and be set, as needed, in accordance with the dynamic range required for the radiation imaging apparatus 100.

The reset signal PRES, the enable signal EN, the clamp signal PCL, the enable signal ENO, the sample/hold signals TN, TS1, and TS2, and the row selection signal VST described above are control signals output from the row selection circuit 120 under the control of the control unit 130. As shown in FIG. 2, these control signals are input from the row selection circuit 120 to transistors and switches corresponding to the pixel 112 via the row control signal line 122.

Figures 4, 5:
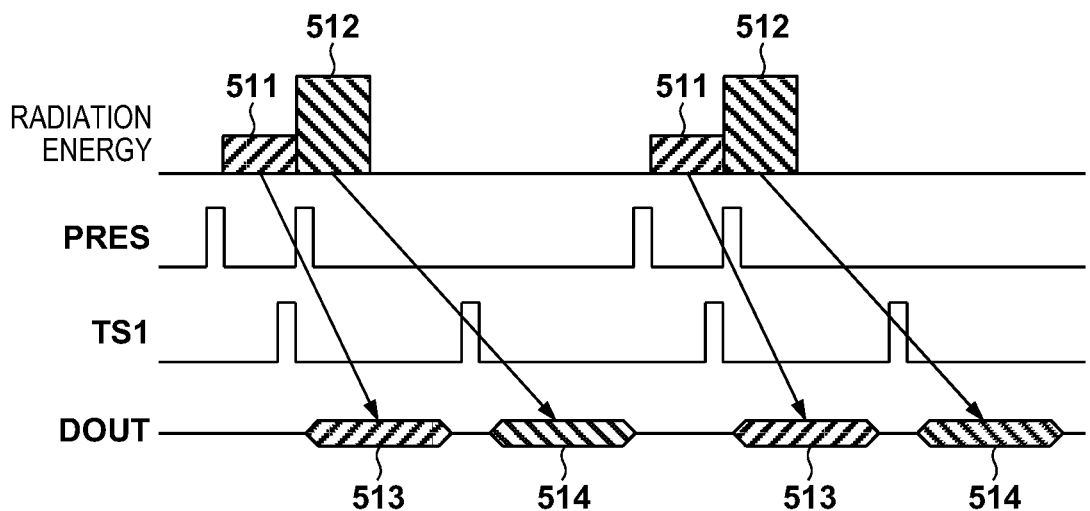
FIG. 4 is a timing chart showing an example of the operation of the radiation imaging system in FIG. 1.
FIG. 5 is a view showing examples of radiation irradiation conditions when obtaining an energy subtraction image by imaging in the radiation imaging system in FIG. 1.

The operation of the radiation imaging system 101 using the radiation imaging apparatus 100 according to this embodiment will be described next with reference to FIG. 4. Referring to FIG. 4, the abscissa represents the time. "radiation energy" represents the waveform of radiation that is emitted from the radiation source 400 and irradiates the radiation imaging apparatus 100. "PRES" represents the reset signal PRES. "TS1" represents the sample/hold signal TS1. "DOUT" represents an output from the AD conversion unit 170.

The system control unit 350 controls the synchronization between the emission of radiation from the radiation source 400 and the operation of the radiation imaging apparatus 100. The control unit 130 controls the operation of the radiation imaging apparatus 100.

First of all, in accordance with user's operations on the system control unit 350, radiation irradiation conditions at the time of obtaining a radiation image by imaging are set, including the energy values of radiation, such as the tube voltage and tube current of the radiation source 400, and the irradiation time of radiation. In a period during which the reset signal PRES is activated, the clamp signal PCL is also activated over a predetermined period, thereby clamping a noise level in the clamp circuit 260. In addition, the conversion element 210 is reset by activating the reset signal PRES over a predetermined period.

Figure 8:
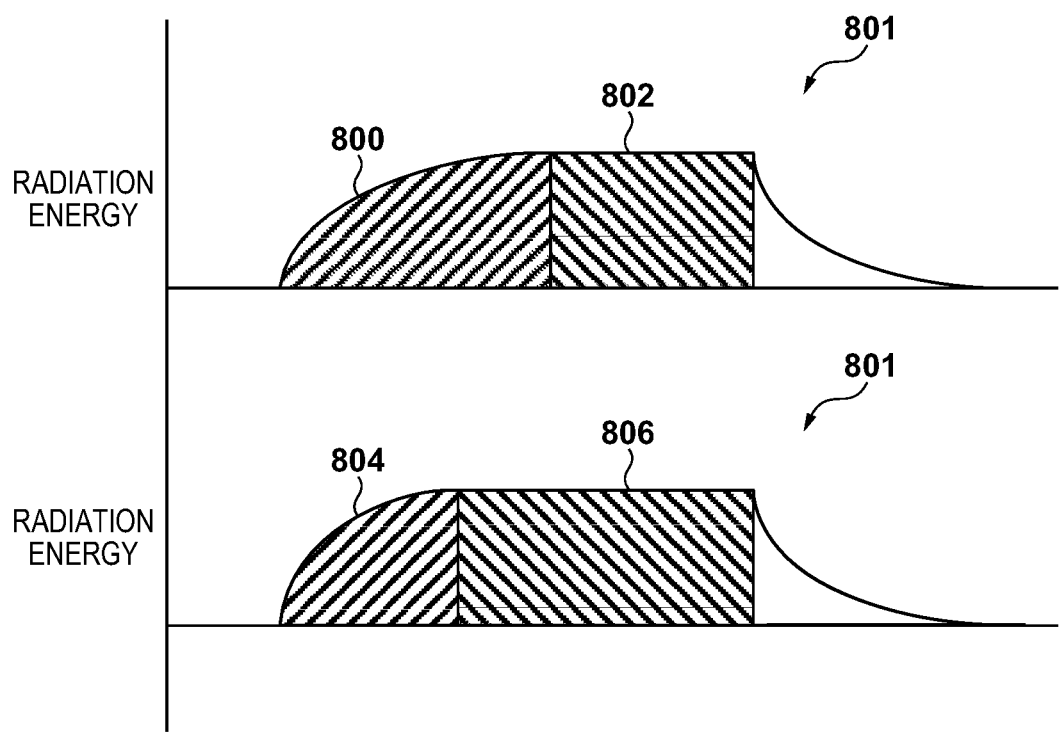
FIG. 8 is a graph showing waveform examples of radiation.

Subsequently, the radiation source 400 emits radiation 511 and radiation 512 having different energy values under the control of the system control unit 350. In this embodiment, the radiation source 400 emits first the radiation 511 having a low energy value and then the radiation 512 having a higher energy value than the radiation 511 under the control of the system control unit 350. However, the emission order of radiations having different energy values is not limited to this. The radiation source 400 may emit radiation having a high energy value first. In addition, the radiation 511 and the radiation 512 may be emitted consecutively over time or there may be time interval between emission of the radiation 511 and the radiation 512. The user may select irradiation conditions for the radiation 511 and the radiation 512 as needed in accordance with an object from an irradiation condition table like that shown in FIG. 5, which is stored in a storage unit 354 provided in the system control unit 350. The radiation imaging apparatus 100 may also include a camera or gage for measuring the thickness of an object. In this case, the control unit 130 may select irradiation conditions concerning the radiation 511 and the radiation 512 from the table in accordance with information such as the detected thickness of the object. Alternatively, for example, in order to select radiation irradiation conditions, an object may be imaged in advance with a low dose to estimate, for example, the thickness of the object from the transmission dose of radiation. The control unit 130 may then select irradiation conditions concerning the radiation 511 and the radiation 512 from the table in accordance with the estimated thickness of the object. In this embodiment, irradiation with radiation is performed twice. However, this is not exhaustive. As shown in FIG. 8, the rising and falling of radiation during one irradiation with radiation 801 may be used to perform imaging with radiation 800 and imaging with radiation 802 before and after the operation of the first sample/hold signal TS1.

In accordance with irradiation with radiations from the radiation source 400, the control unit 130 causes the imaging unit 111 to perform first imaging and second imaging after the first imaging for generation of one energy subtraction image. First of all, the sample/hold circuit 280 samples the image signal generated by the pixel 112 by irradiation with the radiation 511 after irradiation with the radiation 511 and before irradiation with the radiation 512 in accordance with the sample/hold signal TS1 from the control unit 130. Thereafter, the conversion element 210 is reset by activating the reset signal PRES over a predetermined time.

The second imaging is then performed by irradiation with the radiation 512. During this period, the control unit 130 causes the readout circuit 140 to read out the image signal obtained by the first imaging by irradiation with the radiation 512 and held in the sample/hold circuit 280 while the second imaging is performed by irradiation with the radiation 512. Thereafter, the image signal obtained by irradiation with the radiation 511 is output as an image signal 513 via the column selection circuit 150, the amplification unit 160, and the AD conversion unit 170. After the readout circuit 140 reads out the image signal obtained by irradiation with the radiation 512 from the sample/hold circuit 280, the sample/hold circuit 280 samples the image signal generated by the pixel 112 by irradiation with the radiation 512 in accordance with the sample/hold signal TS1. The image signal generated by irradiation with the radiation 512 is processed like the image signal generated by irradiation with the radiation 511 and is output as an image signal 514 from the AD conversion unit 170. The radiation imaging apparatus 100 can shorten the interval between two imaging operations by concurrently performing reading out of the signal obtained by the first imaging and accumulation of the signal obtained by the second imaging in this manner. This makes it possible to improve the performance of the radiation imaging apparatus 100 by providing the sample/hold circuit 280 in obtaining an energy subtraction image of a fast moving object.

The signal processing unit 352 of the system control unit 350 obtains a subtraction image by processing the image signal 513 and the image signal 514 in accordance with an energy subtraction method. In this case, various methods can be used as energy subtraction methods. For example, a bone image and a soft tissue image can be obtained by calculating differences between the radiation image obtained by low-energy radiation (radiation 511) and the radiation image obtained by high-energy radiation (radiation 512). Alternatively, a bone image and a soft tissue image may be obtained by solving non-linear simultaneous equations based on the radiation image obtained by low-energy radiation and the radiation image obtained by high-energy radiation. Alternatively, a contrast medium image and a soft tissue image can be obtained based on the radiation image obtained by low-energy radiation and the radiation image obtained by high-energy radiation. Alternatively, an electron density image and an effective atomic number image can be obtained based on the radiation image obtained by low-energy radiation and the radiation image obtained by high-energy radiation.

A method of generating the radiation irradiation condition table shown in FIG. 5 will be described in detail next. As shown in FIG. 5, radiation irradiation conditions include, for example, tube voltage values and tube current values for setting the energy values of radiations emitted for two imaging operations and the irradiation times of radiation. It is possible to calculate the amounts of noise in energy subtraction images after four arithmetic operations between a high-energy image and a low-energy image according to equations (1), (2), and (3) given below. In this case, let $M_1$ be the pixel value of a high-energy image, $\varepsilon_1$ be the noise value of the high-energy image, $M_2$ be the pixel value of a low-energy image, and $\varepsilon_2$ be the noise value of the low-energy image.

$$(M_1 \pm \varepsilon_1) \pm (M_2 \pm \varepsilon_2) = (M_1 \pm M_2) \pm \sqrt{\varepsilon_1^2 + \varepsilon_2^2} \quad (1)$$

$$(M_1 \pm \varepsilon_1) \times (M_2 \pm \varepsilon_2) = (M_1 \times M_2) \pm \sqrt{(M_2 \times \varepsilon_1)^2 + (M_1 \times \varepsilon_2)^2} \quad (2)$$

$$(M_1 \pm \varepsilon_1)/(M_2 \pm \varepsilon_2) = \left(\frac{M_1}{M_2}\right) \pm \sqrt{\left(\frac{1}{M_2} \times \varepsilon_1\right)^2 + \left(\frac{M_1}{M_2^2} \times \varepsilon_2\right)^2} \quad (3)$$

The following is a case in which bone suppression processing is performed as typical processing of energy subtraction processing in this specification. Bone suppression processing is image processing of removing bone portions from the radiation image obtained by using a low-energy image and a high-energy image. In general, in bone suppression processing, image processing is often performed by using equation (4). In this case, let be the $M_{cor}$ pixel value of an energy subtraction image, $\varepsilon_{cor}$ be the noise value of the energy subtraction image, I be the dose of radiation, and a be a correction coefficient (constant) for weighting a high-energy image and a low-energy image.

$$M_{cor} \pm \varepsilon_{cor} = (M_1 \pm \varepsilon_1) - \alpha \times (M_2 \pm \varepsilon_2) \quad (4)$$

The noise value $\varepsilon_{cor}$ of an energy subtraction image is represented by equation (5) by applying equation (1) to equation (4).

$$\varepsilon_{cor} = \sqrt{\varepsilon_1^2 + (\alpha \times \varepsilon_2)^2} \quad (5)$$

In order to minimize the noise value $\varepsilon_{cor}$ of an energy subtraction image in equation (5) from a relational expression (equation (6)) concerning an arithmetic/geometric average, equation (7) must hold.

$$\varepsilon_1^2 + (\alpha \times \varepsilon_2)^2 \geq 2\alpha \varepsilon_1 \varepsilon_2 \quad (6)$$

$$\varepsilon_1^2 = (\alpha \times \varepsilon_2)^2 \quad (7)$$

That is, equation (8) given below must hold.

$$\varepsilon_1 = \alpha \times \varepsilon_2 \quad (8)$$

$$\varepsilon \propto \sqrt{I} \quad (9)$$

Figure 6:
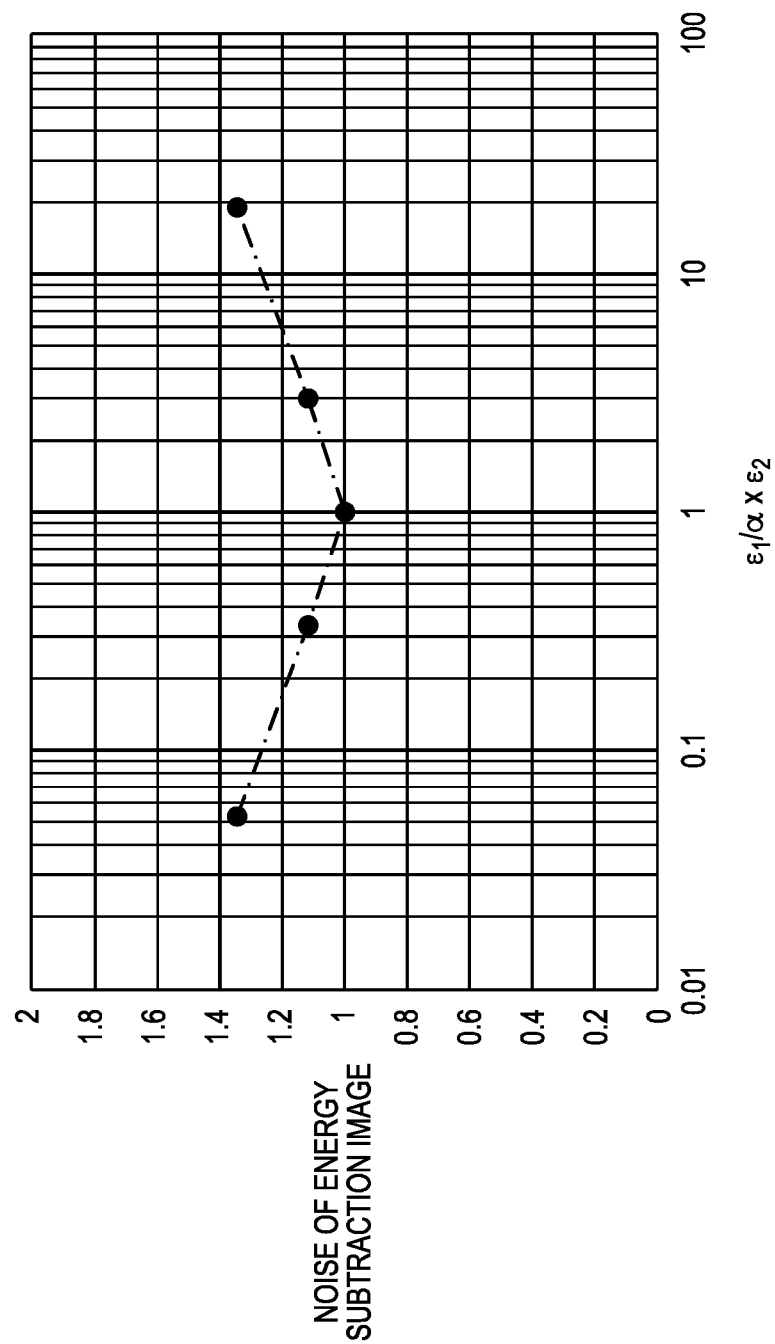
FIG. 6 is a graph showing the relationship between noise in a high-energy image and a low-energy image and noise in an energy subtraction image.

Equation (9) indicates that the noise of a radiation image is proportional to the square root of a transmission dose because the number of arrival radiation particles follows a Poisson distribution. In this case, considering that only the noise of an energy subtraction image is reduced without increasing the exposure dose of an object, it is possible to obtain radiation irradiation conditions by using equations (7) and (9). However, the noise values $\varepsilon_1$ and $\varepsilon_2$ as the amounts of noise in a high-energy image and a low-energy image vary for each object thickness or material. For this reason, it is not always possible to perform imaging under ideal radiation irradiation conditions. Accordingly, for example, a radiation irradiation condition table is generated such that $\varepsilon_1/(\alpha \times \varepsilon_2)$ falls within the range of ⅓ to 3. FIG. 6 is a graph showing the transition of the amount of noise in an energy subtraction image relative to the amount of noise in a low-energy image and the amount of noise in a high-energy image. As is obvious from FIG. 6, setting $\varepsilon_1/(\alpha \times \varepsilon_2)$ within the range of ⅓ to 3 makes it possible to suppress an increase in the amount of noise to about 10% or less from the optimal amount of noise in an energy subtraction image. In this manner, the amount of noise in an image signal is determined based on relational expressions (equations (1), (2), and (3)) concerning error propagation in four arithmetic operations.

Radiation irradiation conditions are set by, for example, user's input to the system control unit 350. The irradiation conditions are transmitted to the control unit 130. The control unit 130 controls the sample/hold circuit 280 to reduce the difference between the amount of noise contained in the image signal obtained by first imaging and the amount of noise contained in the image signal obtained by second imaging in accordance with the radiation irradiation conditions set in advance. More specifically, the control unit 130 controls the timing when the sample/hold circuit 280 samples an image signal by using the sample/hold signal TS1 in order to obtain the image signal generated by irradiation with the radiation 511 in the first imaging. Likewise, the control unit 130 controls the timing when the sample/hold circuit 280 samples an image signal by using the sample/hold signal TS1 in order to obtain the image signal generated by irradiation with the radiation 512 in the second imaging.

As shown in FIG. 8, in the same manner, the rising and falling of radiation during one irradiation with radiation are used to perform imaging with the radiation 800 and imaging with the radiation 802 before and after the operation of the first sample/hold signal TS1. In this case, radiation irradiation conditions include information such as tube voltage values and tube current values for setting the energy values of radiations, the irradiation times of radiation, and temporal changes in radiation energy. Information about temporal changes in the waveform of radiation energy may be stored in the storage unit 354 or the like in advance in accordance with conditions such as a plurality of energy values of radiations. Such information may be read out from the storage unit 354 upon setting of an energy value. Radiation irradiation conditions are set by user's input to the system control unit 350. The irradiation conditions are transmitted to the control unit 130. The control unit 130 controls the sample/hold circuit 280 to reduce the difference between the amount of noise contained in the image signal obtained by the first imaging and the amount of noise contained in the image signal obtained by the second imaging in accordance with radiation irradiation conditions set in advance. The control unit 130 controls the timing when the sample/hold circuit 280 samples an image signal by using the sample/hold signal TS1 and the reset signal PRES so as to reduce the difference between the amounts of noise in accordance with irradiation conditions set in advance. More specifically, the control unit 130 causes the sample/hold circuit 280 to sample the first image signal at the timing of the radiation 800 by using the sample/hold signal TS1 during irradiation with the radiation 801. The control unit 130 then resets the conversion element 210 by using the reset signal PRES. The control unit 130 also causes the sample/hold circuit 280 to sample the second image signal at the timing of the radiation 802 by using the sample/hold signal TS1. For example, the control unit 130 controls the sample/hold circuit 280 to sample the image signal at timings such that the amount of noise in the image signal obtained by low-energy radiation to which a correction coefficient is applied becomes ⅓ times or more and 3 times or less the amount of noise in the image signal obtained by high-energy radiation.

This embodiment has exemplified the form of processing for separating a bone image from a soft tissue image by differential processing for a low-energy image and a high-energy image. However, the present invention is not limited to this form. For example, the present invention can be applied to a case in which a bone image is separated from a soft tissue image by solving non-linear simultaneous equations using a low-energy image and a high-energy image or a case in which an electron density image is separated from an effective atomic number image. In addition, in the embodiment, the energy value of radiation is changed by changing the tube voltage and tube current of the radiation source 400. However, this is not exhaustive. For example, it is possible to obtain images from radiations having different energies by switching between insertion and non-insertion of a beam hardening filter without changing the tube voltage and tube current of the radiation source 400.

In this embodiment, the control unit 130 controls the radiation imaging apparatus 100 to cause the sample/hold circuit 280 to sample image signals in accordance with the amounts of noise contained in the image signals generated by imaging using radiations with two different energies. This makes it possible to suppress noise in an energy subtraction image and obtain an energy subtraction image with high image quality. In addition, the embodiment can be configured to reduce noise in a subtraction image by only holding a radiation irradiation condition table in the storage unit 354 without increasing an exposure dose. This is advantageous in facilitating system construction because there is no need to add any special arrangement to the radiation imaging system 101 except for holding an irradiation condition table.

Figure 7:
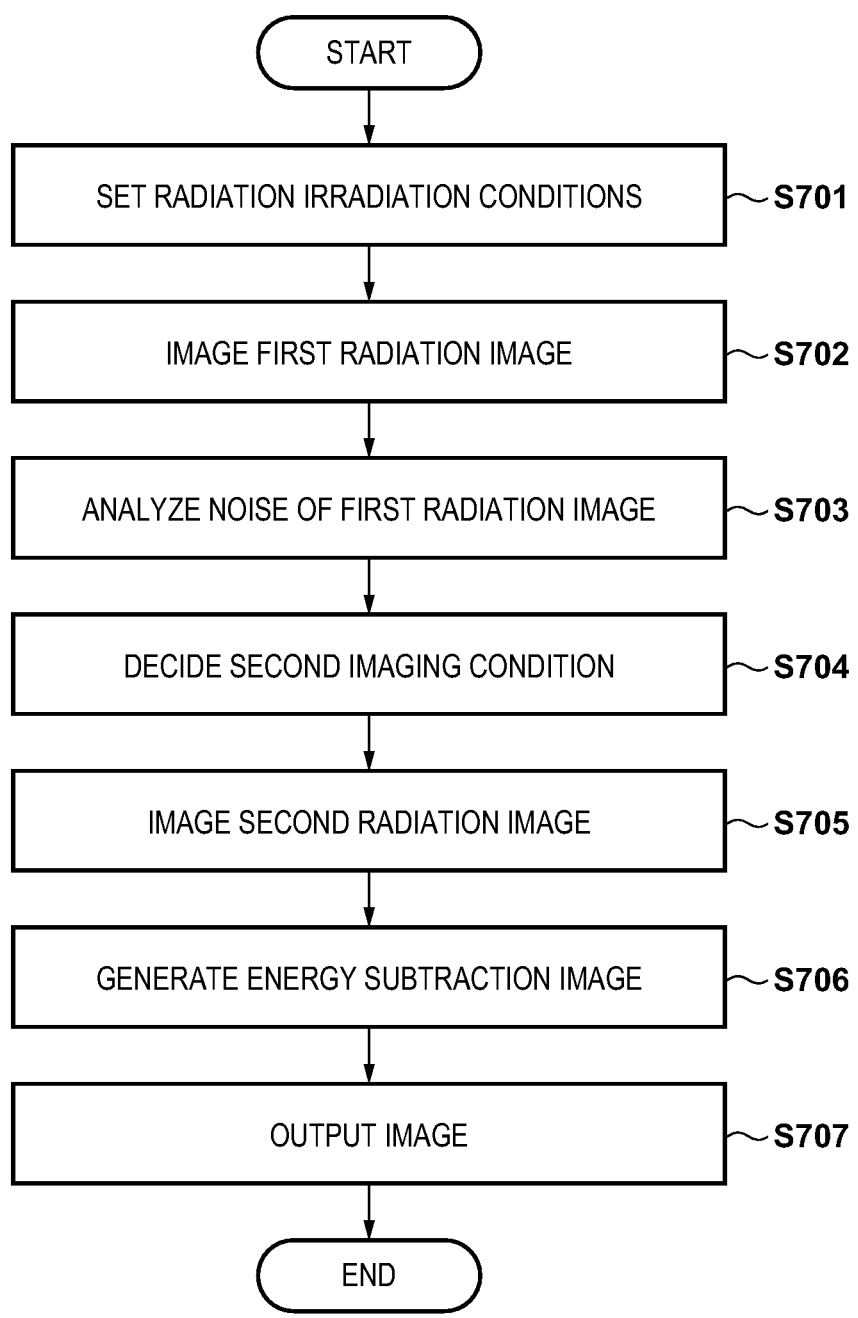
FIG. 7 is a flowchart for obtaining an energy subtraction image by imaging using the radiation imaging apparatus in FIG. 1.

The arrangement and operation of a radiation imaging apparatus according to an embodiment of the present invention will be described with reference to FIG. 7. FIG. 7 is a flowchart showing the processing from imaging of an object using a radiation imaging apparatus 100 according to the second embodiment of the present invention to displaying of an energy subtraction image. The arrangements of the radiation imaging apparatus 100 and a radiation imaging system 101 may be the same as those of the first embodiment described above, and hence a description will be omitted.

In step S701, in accordance with user's operations on a system control unit 350, radiation irradiation conditions at the time of imaging are set, including the energy values of radiation, such as the tube voltage and tube current of a radiation source 400, the irradiation time of radiation, and temporal changes in the waveform of radiation applied. When the radiation imaging apparatus 100 includes a storage unit 354, the user may select appropriate conditions from the radiation irradiation conditions stored in the storage unit 354 in accordance with an object. When irradiation with radiation is to be performed once, conditions are read out from the storage unit 354 and set, including the energy value of radiation and a temporal change in waveform, which correspond to the characteristics of the radiation source 400, and the irradiation time of radiation. When irradiation with radiation is to be performed twice, appropriate conditions are read out from the above irradiation condition table in the storage unit 354 and set. In addition, the radiation imaging apparatus 100 may include a camera or gage for measuring the thickness of an object. In this case, a control unit 130 may select appropriate conditions from the radiation irradiation conditions stored in the storage unit 354 in accordance with the detected thickness of the object. Alternatively, for example, in order to select radiation irradiation conditions, an object may be imaged in advance with a low dose to estimate, for example, the thickness of the object from the transmission dose of radiation. The control unit 130 may then determine appropriate radiation irradiation conditions from the estimated object thickness. Upon setting radiation irradiation conditions, the control unit 130 determines the timing when a sample/hold circuit 280 samples an image signal in the first imaging in accordance with the set irradiation conditions. At this time, the control unit 130 may also tentatively determine the timing when the sample/hold circuit 280 samples an image signal in the second imaging.

After radiation irradiation conditions are set in step S701, the first imaging is performed to obtain a radiation image in step S702. The generated image signal is output to a signal processing unit 352. In step S703, the control unit 130 analyzes the amount of noise contained in the image signal for the radiation image obtained by the first imaging obtained in step S702 and output to the signal processing unit 352. The control unit 130 may analyze an image signal of a predetermined region of an imaging unit 111 as a region of interest where the amount of noise is analyzed. The control unit 130 may select an image signal of an arbitrary portion of the imaging unit 111 by using a region extraction technique or the like. For example, the control unit 130 may select, as a predetermined region, a region with a small transmission dose, such as a lumbar vertebra having a thick bone. Alternatively, for example, a suitable filter or the like may be provided in the visual field of the imaging unit 111 to let the user select the place provided with the filter as a predetermined region. Alternatively, when a filter or the like is provided in the visual field, the control unit 130 may recognize the place provided with the filter as a region with a small transmission dose and select the region as a predetermined region. The control unit 130 determines the amount of noise contained in the image signal of the radiation image obtained by the first imaging by performing processing such as obtaining the standard deviation (noise) of an image signal, of the image signal of the high-energy image, which corresponds to the predetermined region.

In step S704, the control unit 130 determines a second imaging condition, more specifically the timing of sampling an image signal, based on the amount of noise determined from the analysis result of the amount of noise contained in the radiation image obtained by the first imaging in step S703. When the timing of the second imaging has been tentatively determined in step S701, the control unit 130 may correct the timing of sampling in accordance with the determined amount of noise. The timing of sampling the image signal obtained by the second imaging is obtained to minimize the noise of an energy subtraction image by the method described above in the first embodiment. In this manner, in this embodiment, the control unit 130 also determines the timing when the sample/hold circuit 280 samples an image signal, based on the amount of noise decided based on relational expressions (equations (1), (2), and (3)) concerning error propagation in the four basic arithmetic operations.

Upon determining the timing of sampling in the second imaging, the control unit 130 controls the imaging unit 111 to perform the second imaging in step S705. At this time, the control unit 130 may control an AEC (Auto Exposure Control) function of stopping irradiation with radiation when a desired transmission dose is reached or the dose of radiation applied by using a phototimer or the like. In this case, when the transmission dose of a region set in advance by the user or the like reaches a desired dose, the control unit 130 may output, to the system control unit 350, a signal for stopping irradiation with radiation from the radiation source 400. In accordance with this signal, the system control unit 350 controls the radiation source 400 to stop irradiation with radiation.

In step S706, the signal processing unit 352 performs energy subtraction processing by using the image signals obtained by two imaging operations and output from the imaging unit 111. In step S707, the energy subtraction image having undergone the energy subtraction processing is output from the signal processing unit 352 and displayed on a display device (not shown) such as a display. At this time, in addition to the energy subtraction image, for example, radiation images obtained by imaging operations with different radiation energy values may be output from the signal processing unit 352 and displayed on the display device.

In this embodiment, the amount of noise contained in the image signal generated by the first imaging is determined. Thereafter, the timing when the sample/hold circuit samples the image signal obtained by the second imaging is set in accordance with the amount of noise. This makes it possible to suppress noise contained in an energy subtraction image more than in the first embodiment and obtain an energy subtraction image with high image quality. However, the signal processing unit 352 needs to analyze the radiation image obtained by the first imaging, and hence the arrangement of the radiation imaging system 101 can be complicated as compared with the first embodiment. In addition, in the embodiment, communication between the control unit 130 and the signal processing unit 352 can increase as compared with the first embodiment. Accordingly, a functional portion, of the signal processing unit 352, which analyzes the amount of noise in a radiation image may be provided in, for example, the radiation imaging apparatus 100 or the control unit 130.

In the first and second embodiments each have exemplified the case in which an energy subtraction image is generated from two radiation images. However, an energy subtraction image may be generated from three or more radiation images obtained by three or more imaging operations. In this case as well, the control unit 130 may control the timing of sampling the image signal obtained by each imaging operation so as to reduce the amount of noise in the energy subtraction image generated in the above manner.

The arrangement and operation of a radiation imaging apparatus according to the third embodiment of the present invention will be described with reference to FIGS. 8 to 11. In the two embodiments described above, the control unit 130 controls the timing when the sample/hold circuit 280 samples image signals so as to reduce the amounts of noise in two obtained image signals. The third embodiment will exemplify a method of generating an energy subtraction image with a small amount of noise from a plurality of image signals obtained by a plurality of times of imaging during one irradiation with radiation using the sample/hold circuit 280. The arrangements of a radiation imaging apparatus 100 and a radiation imaging system 101 may be the same as those of the first and second embodiments, and hence a description of the arrangement will be omitted.

As shown in FIG. 8, consider a case in which the rising and falling of radiation during one irradiation with radiation 801 are used to perform imaging a plurality of times during one irradiation with radiation as irradiation with radiations with different energies before and after an operation using a sample/hold signal TS1 and a reset signal PRES. As shown in FIG. 8, depending on the timing of the sample/hold signal TS1, the dose and energy value of radiation applied in each imaging change. In general, the amount of noise in a subtraction image decreases with an increase in the energy difference between two radiation images.

As shown on the upper side of FIG. 8, consider a case in which the control unit 130 controls the timing of sampling such that one irradiation with the radiation 801 is performed as a combination of irradiation with radiation 800 and irradiation with radiation 802. In this case, obtaining an image signal for generating a radiation image by using the entire rising waveform of radiation like the radiation 800 can save a dose. However, this reduces the energy difference from the radiation image generated from the image signal obtained with the radiation 802.

As shown on the lower side of FIG. 8, consider a case in which the control unit 130 controls to perform sampling such that one irradiation with the radiation 801 is performed as a combination of irradiation with radiation 804 and irradiation with radiation 806. In this case, obtaining an image signal for generating a radiation image midway along the rising waveform of radiation like the radiation 804 can increase the energy difference from the radiation image generated from the image signal obtained by the radiation 806. However, this can reduce the dose of radiation 804 and increase the amount of noise in an energy subtraction image. This makes it necessary to properly adjust the energy difference between two radiation images and the amounts of noise contained in the respective image signals. A method of adjusting the energy difference between two radiation images and the amounts of noise will be described in detail with reference to FIG. 9.

Figure 9:
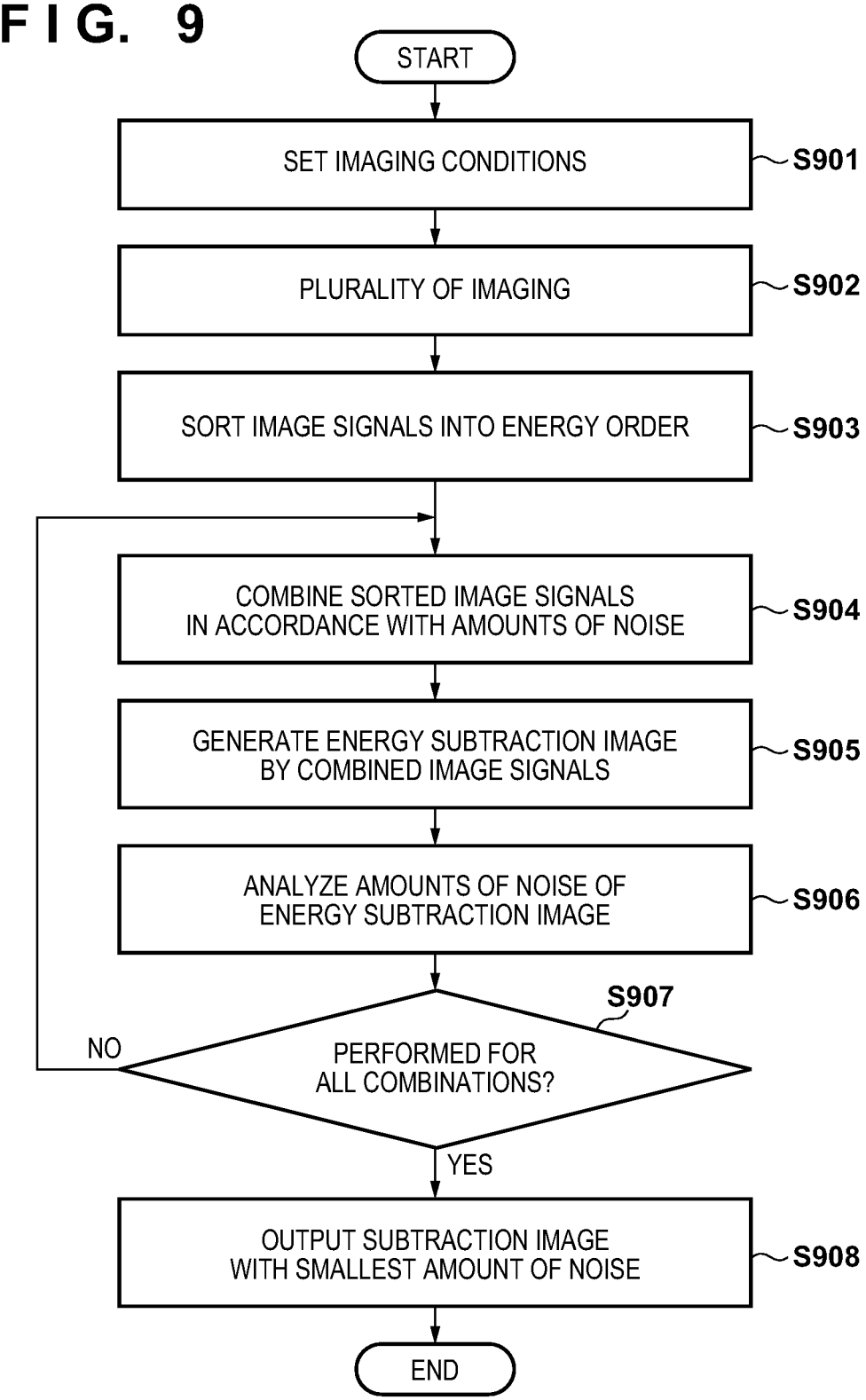
FIG. 9 is a flowchart for obtaining an energy subtraction image by imaging using the radiation imaging apparatus in FIG. 1.

FIG. 9 is a flowchart showing the processing from imaging of an object using the radiation imaging apparatus 100 according to the third embodiment of the present invention to displaying of an energy subtraction image. In step S901, imaging conditions are set. The imaging conditions include information such as the energy value of radiation, the irradiation time of radiation, and a temporal change in the waveform of radiation energy. The imaging conditions also include the number of times of imaging during one irradiation with radiation.

Figure 10:
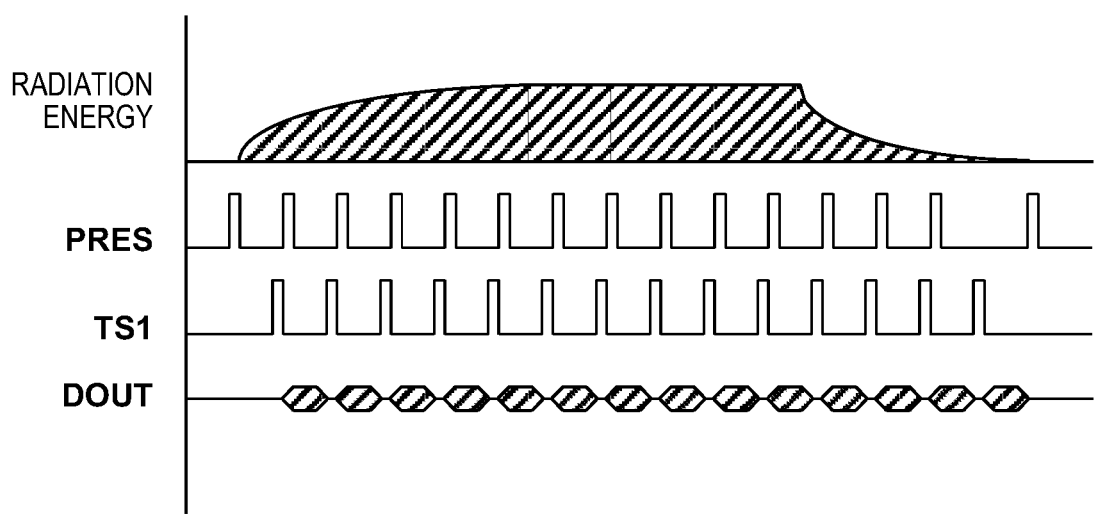
FIG. 10 is a timing chart showing an example of the operation of the radiation imaging system in FIG. 1.

After the imaging conditions are set, a radiation source 400 emits radiation in accordance with the set conditions in step S902. As shown in FIG. 10, the control unit 130 of the radiation imaging apparatus 100 causes an imaging unit 111 to perform imaging a plurality of times during one irradiation with radiation. The control unit 130 causes the readout circuit 140 to read out a plurality of image signals sampled by sample/hold circuits 270, 280 and 290 in each of a plurality of times of imaging. The radiation imaging apparatus 100 includes the sample/hold circuits 270, 280, and 290. Accordingly, the radiation imaging apparatus 100 can shorten the interval between two imaging operations by concurrently performing reading out of the signal obtained by the first imaging and accumulation of the signal obtained by the second imaging. In addition, including the sample/hold circuits 270, 280, and 290 allows the radiation imaging apparatus 100 to obtain more image signals at shorter intervals during one irradiation with radiation.

The image signals generated by a plurality of times of imaging and read out by a readout circuit 140 are transferred to a signal processing unit 352. The arrangement shown in FIG. 10 is configured to obtain 14 image signals by performing 14 imaging operations during one irradiation with radiation. However, the number of image signals obtained is not limited to this. The number of image signals obtained may be 13 or less or 15 or more. In addition, imaging need not be performed at equal intervals, and the sample/hold circuits 270, 280, and 290 can sample image signals at arbitrary timings under the control of the control unit 130.

Figure 11:
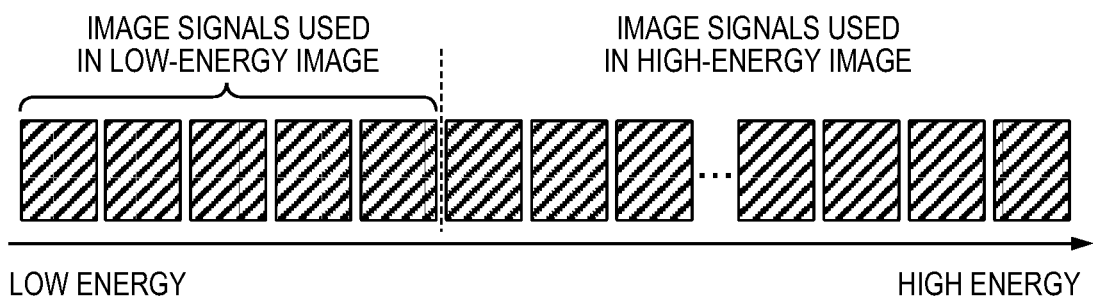
FIG. 11 is a view schematically showing how image signals are divided to high-energy image signals and low-energy image signals.

In step S903, as shown in FIG. 11, the signal processing unit 352 sorts obtained radiation images based on information about radiation energy. For example, the signal processing unit 352 may sort a plurality of image signals according to the order of the differences between high-energy portions and low-energy portions of the plurality of image signals as information about radiation energy. In this case, if an object is the human body, the differences in transmittance between bone portions and fat portions may be used as information about radiation energy. In addition, the signal processing unit 352 may sort a plurality of image signals according to the order of the energy values of high-energy portions of radiation of the plurality of image signals as information about radiation energy. In this case, the energy values of high-energy portions may be the pixel values of pixels corresponding to highest-energy portions of the obtained image signals. In addition, for example, the energy value of a highest-energy portion may be the average value of the pixel values of pixels corresponding to 20% of the highest-energy portion of an obtained image signal.

The first image signal obtained by imaging is formed from a rising portion of radiation and hence can be an image signal of a low-energy image. On the other hand, an image signal obtained by imaging after the rising of the radiation can be an image signal of a high-energy image. In addition, the last image signal obtained by imaging is formed from a falling portion of the radiation and hence can be an image signal of a low-energy image.

In step S904, the signal processing unit 352 divides the plurality of sorted image signals into image signals used for a low-energy image and image signals used for a high-energy image. The divided image signals are combined into an image signal for a low-energy image and an image signal for a high-energy image. The image signal for the low-energy image and the image signal for the high-energy image are generated by averaging or weighting and averaging signals, of a plurality of image signals, which are combined into an image signal for a low-energy image and an image signal for a high-energy image.

When dividing a plurality of sorted image signals, the signal processing unit 352 may divide the signals into two groups by using an arbitrary energy value as a threshold. In addition, the signal processing unit 352 may divide image signals according to the amounts of noise contained in the respective image signals in consideration of an energy subtraction image obtained in the subsequent step. For example, image signals may be divided such that the difference between the amounts of noise respectively contained in a combined image signal for a low-energy image and a combined image signal for a high-energy image falls within a predetermined range. For example, as described above, a plurality of image signals may be divided based on relational expressions concerning error propagation such that the amount of noise contained in a combined image signal for a low-energy image becomes ⅓ times or more and 3 times or less the amount of noise contained in an image signal for a high-energy image. At this time, a plurality of combinations of combined image signals for low-energy images and combined image signals for high-energy images may be generated, with differences in the amount of noise between the respective combined signals falling within a predetermined range. The following is a case in which a plurality of combinations are generated.

After image signals are combined, energy subtraction images are generated in accordance with the respective combinations of combined image signals for low-energy images and combined image signals for high-energy images in step S905. In step S906, the signal processing unit 352 analyzes the amounts of noise contained in the respective generated energy subtraction images by using, for example, the standard deviations of the pixel values of predetermined portions of the respective energy subtraction images. For example, the signal processing unit 352 may select a region with a small transmission dose as a predetermined region. The signal processing unit 352 can analyze the amount of noise by using the same method as that described in the second embodiment. Each analysis value is stored in a storage unit 354 so as to be referred to later.

In step S907, the signal processing unit 352 determines whether energy subtraction images have been generated from all combinations of the obtained image signals for low-energy images and the obtained image signals for high-energy images. If NO in step S907, the process returns to step S904 to generate an energy subtraction image by a combination pattern from which no energy subtraction image has been generated. If energy subtraction images have been generated from all combinations, the process shifts to step S908. Note however that energy subtraction images are generated from arbitrary combinations but need not be generated from all combinations.

In step S908, the signal processing unit 352 outputs an energy subtraction image, of the energy subtraction images generated from the plurality of combinations, which contains the smallest amount of noise. The output energy subtraction image is displayed on a display device (not shown) such as a display.

In this embodiment, the signal processing unit 352 determines combinations for combining a plurality of image signals so as to minimize the amount of noise contained in an energy subtraction image that is actually output. This makes it possible to obtain an energy subtraction image in which noise has been reliably reduced. However, in the embodiment, because the signal processing unit 352 performs many image processing operations, it can take much time until a subtraction image is displayed after imaging. In addition, in the embodiment, because it is necessary to perform many imaging operations and output a plurality of image signals to the signal processing unit 352, the signal processing unit 352 may be provided in the radiation imaging apparatus 100. Furthermore, in the embodiment, when a reset operation is performed during a plurality of imaging operations, the reset operation period becomes ineffective exposure that makes no contribution to the generation of an image signal. Accordingly, the sample/hold circuits 270, 280, and 290 may sample generated signals a plurality of times without performing any reset operation, and differences between the respective signals may be used as image signals.

The above means provide a technique advantageous in improving the image quality of an energy subtraction image in a radiation imaging apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
an imaging unit including a plurality of pixels and a control unit;
each of the plurality of pixels including a conversion unit configured to generate an image signal corresponding to incident radiation and a sample/hold circuit configured to sample an image signal generated by the conversion unit; and
the control unit being configured to (i) cause the imaging unit to perform first imaging and second imaging after the first imaging to generate one energy subtraction image, (ii) control a timing of causing the sample/hold circuit in the first imaging to sample a first image signal, and (iii) control a timing of causing the sample/hold circuit in the second imaging to sample a second image signal using an amount of noise contained in the first image signal, wherein
the amount of noise is determined based on an image signal of at least a part of the first image signal.

2. The radiation imaging apparatus according to claim 1, wherein the radiation irradiation conditions include energy values of radiations and radiation irradiation times in the first imaging and the second imaging.

3. The radiation imaging apparatus according to claim 1, wherein the control unit is configured to cause the imaging unit to perform the first imaging and the second imaging during one irradiation with radiation, and
the first imaging is performed using radiation having an energy value higher than the second imaging.

4. The radiation imaging apparatus according to claim 1, wherein the radiation irradiation conditions include a temporal change in energy of radiation.

5. The radiation imaging apparatus according to claim 1, further comprising a readout circuit, wherein
the control unit is configured to cause the readout circuit to read out the first image signal held in a sample/hold circuit during the second imaging.

6. The radiation imaging apparatus according to claim 1, wherein the control unit determines the amount of noise contained in the first image signal based on a standard deviation of the image signal, of the first image signal, that corresponds to the predetermined region.

7. The radiation imaging apparatus according to claim 6, wherein the image signal of the predetermined region includes an image signal of a region with a small transmission dose.

8. The radiation imaging apparatus according to claim 1, wherein the amount of noise is determined based on a relational expression concerning error propagation in four arithmetic operations.

9. The radiation imaging apparatus according to claim 1, further comprising a signal processing unit configured to apply a correction coefficient to the second image signal when generating an energy subtraction image, wherein
the control unit is configured to control the sample/hold circuit to sample the first image signal and the second image signal at timings when an amount of noise in the second image signal to which the correction coefficient is applied becomes $\frac{1}{3}$ to 3 times an amount of noise in the first image signal.

10. A radiation imaging system, comprising:
the radiation imaging apparatus according to claim 1; and
a radiation source configured to emit radiation.

11. The radiation imaging apparatus according to claim 1, wherein the control unit is configured to (i) control a timing of causing the sample/hold circuit in the first imaging to sample the first image signal in accordance with a thickness of an object, and (ii) control the timing of causing the sample/hold circuit in the second imaging to sample the second image signal in accordance with the amount of noise and the thickness of the object.

12. A radiation imaging apparatus, comprising:
an imaging unit including a plurality of pixels, a readout circuit, a signal processing unit, and a control unit;
each of the plurality of pixels including a conversion unit configured to generate an image signal corresponding to incident radiation and a sample/hold circuit configured to sample an image signal generated by the conversion unit;
the control unit being configured to (i) cause the imaging unit to perform imaging a plurality of times during one irradiation with radiation and (ii) cause the readout circuit to read out a plurality of image signals sampled by the sample/hold circuit in each of the plurality of times of imaging, and
the signal processing unit being configured to (i) determine an amount of noise contained in each of a plurality of image signals read out by the readout circuit based on an image signal, of each of the plurality of image signals, that corresponds to a predetermined region, (ii) divide the plurality of image signals into a first group of image signals and a second group of image signals in accordance with information of energy of radiation corresponding to a pixel value of each of the plurality of image signals and the amount of noise contained in each of the plurality of image signals, (iii) generate a first image signal by using the first group of image signals, and a second image signal by using the second group of image signals, and (iv) generate an energy subtraction image by using the first image signal and the second image signal.

13. The radiation imaging apparatus according to claim 12, wherein the signal processing unit is configured to divide the plurality of image signals into a plurality of groups of image signals including the first group of image signals and the second group of the image signals, and generate a plurality of generated image signals including the first image signal and the second image signal by using each of the plurality of groups of image signals, and the signal processing unit is configured to generate a plurality of combinations of generated image signals from the plurality of generated image signals, generate a plurality of energy subtraction images from the plurality of combinations, and output an image that has a smallest amount of noise contained of the plurality of energy subtraction images.

14. The radiation imaging apparatus according to claim 12, wherein the signal processing unit is configured to divide the plurality of image signals into the first group of image signals and the second group of image signals in accordance with an order of differences between a pixel value of a pixel corresponding to high-energy portions and a pixel value of a pixel corresponding to low-energy portions of radiations of the plurality of image signals.

15. The radiation imaging apparatus according to claim 12, wherein the signal processing unit is configured to divide the plurality of image signals into the first group of image signals and the second group of the image signals in accordance with an order of pixel values of a pixel corresponding to high-energy portions of radiations of the plurality of image signals.

16. The radiation imaging apparatus according to claim 12, wherein the signal processing unit is configured to divide the plurality of image signals into the first group of image signals and the second group of image signals so as to make an amount of noise in the first image signal become ⅓ to 3 times an amount of noise in the second image signal.

17. The radiation imaging apparatus according to claim 16, which is configured to determine amounts of noise in the first image signal and the second image signal based on a relational expression concerning error propagation in four arithmetic operations.

18. The radiation imaging apparatus according to claim 12, which is configured to generate the first image signal and the second image signal by averaging, or weighting and averaging signals of the plurality of image signals.

19. A control method of a radiation imaging apparatus comprising an imaging unit including a plurality of pixels and a control unit, each of the plurality of pixels including a conversion unit configured to generate an image signal corresponding to incident radiation and a sample/hold circuit configured to hold an image signal generated by the conversion unit, the method comprising the steps of:

causing the imaging unit to perform first imaging and second imaging after the first imaging to generate one energy subtraction image;

the control unit controlling (i) a timing of causing the sample/hold circuit in the first imaging to sample a first image signal and (ii) a timing of causing the sample/hold circuit in the second imaging to sample a second image signal using an amount of noise contained in the first image signal, wherein the amount of noise is determined based on an image signal of at least a part of the first image signal.

20. A non-transitory computer-readable storage medium storing a program for causing a computer to execute the method according to claim 19.

\* \* \* \* \*